US006696444B2

United States Patent
Carling et al.

(10) Patent No.: US 6,696,444 B2
(45) Date of Patent: Feb. 24, 2004

(54) IMIDAZO-TRIAZINE DERIVATIVES AS LIGANDS FOR GABA RECEPTORS

(75) Inventors: William Robert Carling, Bishops Stortford (GB); David James Hallett, Watford (GB); Michael Geoffrey Neil Russell, Welwyn Garden City (GB); Leslie Joseph Street, Little Hallingbury (GB)

(73) Assignee: Merck Sharpe & Dohme, Hoddesdon (GB)

( * ) Notice: Subject to any disclaimer, the term of this patent is extended or adjusted under 35 U.S.C. 154(b) by 0 days.

(21) Appl. No.: 10/463,025

(22) Filed: Jun. 17, 2003

(65) Prior Publication Data

US 2003/0216395 A1 Nov. 20, 2003

Related U.S. Application Data

(62) Division of application No. 10/195,274, filed on Jul. 15, 2002, now Pat. No. 6,617,326.

(30) Foreign Application Priority Data

Jul. 16, 2001 (GB) .............................................. 0117277

(51) Int. Cl.⁷ ............................................... A61K 31/53
(52) U.S. Cl. ....................................................... 514/243
(58) Field of Search ........................................... 514/243

(56) References Cited

U.S. PATENT DOCUMENTS 3,422,194 A    1/1969   Loev ........................... 544/184

FOREIGN PATENT DOCUMENTS

| WO | WO 98/34923 A1 | 8/1998 |
| WO | WO 00/78728 A1 | 12/2000 |
| WO | WO 01/18000 A1 | 3/2001 |
| WO | WO 01/38326 A2 | 5/2001 |
| WO | WO 01/90108 A1 | 11/2001 |
| WO | WO 02/10170 A1 | 2/2002 |
| WO | WO 02/38568 A1 | 5/2002 |
| WO | WO 02/38569 A1 | 5/2002 |
| WO | WO 02/074773 A1 | 9/2002 |

*Primary Examiner*—John M. Ford
(74) *Attorney, Agent, or Firm*—J. Eric Thies; Melvin Winokur

(57) ABSTRACT

A class of 7-phenylimidazo[1,2-b][1,2,4]triazine derivatives, substituted at the meta position of the phenyl ring by a (cyano)(fluoro)phenyl moiety, being selective ligands for $GABA_A$ receptors, in particular having good affinity for thee α2 and/or α3 subunit thereof, are accordingly of benefit in the treatment and/or prevention of adverse conditions of the central nervous system, including anxiety and convulsions.

9 Claims, No Drawings

IMIDAZO-TRIAZINE DERIVATIVES AS LIGANDS FOR GABA RECEPTORS

CROSS REFERENCE TO RELATED APPLICATIONS

This application is a division of application Ser. No. 10/195,274, filed Jul. 15, 2002, now U.S. Pat. No. 6,617,326, which claims priority under 35 U.S.C. §119 from GB Application No. 0117277.4, filed Jul. 16, 2001.

The present invention relates to a class of substituted imidazo-triazine derivatives and to their use in therapy. More particularly, this invention is concerned with imidazo[1,2-b][1,2,4]triazine analogues which are substituted in the 7-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta \gamma 1$, $\alpha 2\beta 2/3\gamma 2$, $\alpha 3\beta\gamma 2/3$, $\alpha 4\beta\delta$, $\alpha 5\beta 3\gamma 2/3$, $\alpha 6\beta\gamma 2$ and $\alpha 6\beta\delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse and dependency, including alcohol withdrawal. Selective ligands for $GABA_A$ receptors may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

The present invention provides a class of imidazo-triazine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of zero or weak (positive or negative) efficacy at the α1 subunit and a full or partial agonist profile at the α2 and/or α3 subunit.

The present invention provides a compound of formula I, or a pharmaceutically acceptable salt thereof:

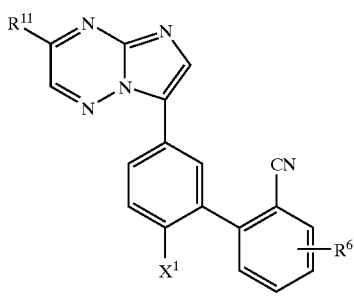

(I)

wherein

X$^1$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, heteroaryl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl;

R$^5$ represents hydrogen, C$_{1-6}$ alkyl, hydroxy(C$_{1-6}$)alkyl or di(C$_{1-6}$)alkylamino(C$_{1-6}$)alkyl; and R$^6$ represents fluoro.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Suitable alkyl groups include straight-chained and branched alkyl groups containing from 1 to 6 carbon atoms.

Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy" are to be construed accordingly.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The term "halogen" as used herein includes fluorine, chlorine, bromine and iodine, especially fluoro or chloro.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In one embodiment, X$^1$ represents hydrogen. In another embodiment, X$^1$ represents fluoro.

Suitably, R$^4$ represents hydrogen or methyl.

Suitably, R$^5$ represents hydrogen, methyl, ethyl, hydroxyethyl or dimethylaminoethyl. Particular values of R$^5$ include hydrogen, hydroxyethyl and dimethylaminoethyl.

Where R$^{11}$ represents heteroaryl, this group is suitably furyl.

Illustrative values of R$^{11}$ include hydrogen, methyl, fluoromethyl, difluoromethyl, trifluoromethyl, hydroxymethyl, difluoroethyl, hydroxyethyl, fluoropropyl, hydroxypropyl, tert-butyl, furyl, chloro, methoxy, formyl, acetyl, methoxycarbonyl and —CR$^2$=NOR$^3$, in which R$^2$ and R$^3$ are as defined above.

Specific values of R$^{11}$ include hydrogen, methyl, difluoroethyl (especially 1,1-difluoroethyl), fluoropropyl (especially 2-fluoroprop-2-yl), hydroxypropyl (especially 2-hydroxyprop-2-yl), tert-butyl and trifluoromethyl.

In one embodiment, R$^{11}$ represents methyl. In another embodiment, R$^{11}$ represents trifluoromethyl. In a further embodiment, R$^{11}$ represents 2-hydroxyprop-2-yl. In an additional embodiment, R$^{11}$ represents 2-fluoroprop-2-yl.

The fluorine atom R$^6$ is favourably attached to the phenyl ring at the 4-, 5- or 6-position (relative to the cyano group at position 2), preferably at the 6-position.

Specific compounds within the scope of the present invention include:

4,2'-difluoro-5'-[3-(1-fluoro-1-methylethyl)imidazo[1,2-b][1,2,4]triazin-7-yl]biphenyl-2-carbonitrile;
5,2'-difluoro-5'-(3-trifluoromethylimidazo[1,2-b][1,2,4]triazin-7-yl)-biphenyl-2-carbonitrile;
4,2'-difluoro-5'-[3-(1-hydroxy-1-methylethyl)imidazo [1,2-b][1,2,4]triazin-7-yl]biphenyl-2-carbonitrile;
4-fluoro-3'-[3-(1-hydroxy-1-methylethyl)imidazo [1,2-b][1,2,4]triazin-7-yl]-biphenyl-2-carbonitrile;
6,2'-difluoro-5'-[3-(1-hydroxy-1-methylethyl)imidazo [1,2-b][1,2,4]triazin-7-yl]biphenyl-2-carbonitrile;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 50 nM or less, preferably 10 nM or less, and more preferably 5 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking-tests (cf Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums; and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula II with a compound of formula III:

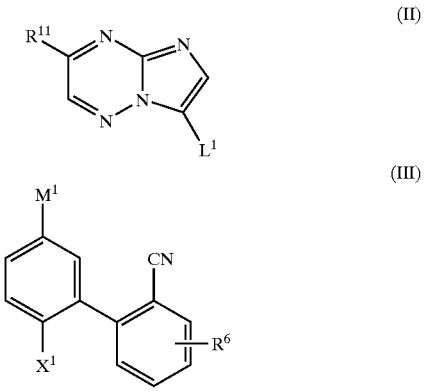

wherein $X^1$, $R^{11}$ and $R^6$ are as defined above, $L^1$ represents a suitable leaving group, and $M^1$ represents a boronic acid moiety —B(OH)₂ or a cyclic ester thereof formed with an organic diol, e.g. pinacol or neopentyl glycol, or $M^1$ represents —Sn(Alk)₃ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds II and III is suitably tetrakis(triphenylphosphine)-palladium(0). The reaction is conveniently carried out at an elevated temperature in a solvent such as N,N-dimethylacetamide, 1,2-dimethoxyethane, tetrahydrofuran or 1,4-dioxane, advantageously in the presence of potassium phosphate, sodium carbonate or copper(I) iodide. Alternatively, the transition metal catalyst employed may be dichloro[1,1'-bis(diphenylphosphino)ferrocene]palladium(II), in which case the reaction may conveniently be carried out at an elevated temperature in a solvent such as N,N-dimethylformamide, typically in the presence of potassium phosphate.

In an alternative procedure, the compounds according to the present invention may be prepared by a process which comprises reacting a compound of formula IV with a compound of formula V:

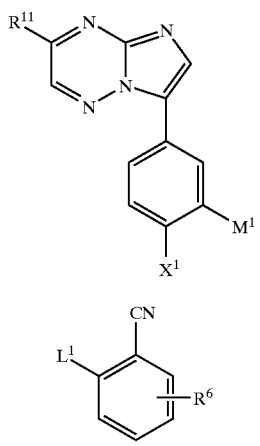

(IV)

(V)

wherein $X^1$, $R^{11}$, $R^6$, $L^1$ and $M^1$ are as defined above; in the presence of a transition metal catalyst; under conditions analogous to those described above for the reaction between compounds II and III.

Where $M^1$ in the intermediates of formula III and IV above represents a boronic acid moiety —$B(OH)_2$ or a cyclic ester thereof formed with pinacol or neopentyl glycol, the relevant compound III or IV may be prepared by reacting bis(pinacolato)diboron or bis(neopentyl glycolato)diborane respectively with a compound of formula VI or VII:

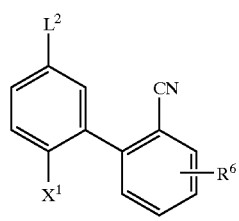

(VI)

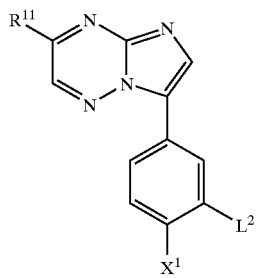

(VII)

wherein $X^1$, $R^{11}$ and $R^6$ are as defined above, and $L^2$ represents hydroxy or a suitable leaving group; in the presence of a transition metal catalyst.

Where $L^2$ represents a leaving group, this is typically trifluoromethanesulfonyloxy (triflyloxy); or a halogen atom such as bromo.

The transition metal catalyst of use in the reaction between bis(pinacolato)diboron or bis(neopentyl glycolato)diborane and compound VI or VII is suitably dichloro[1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where $L^2$ in the intermediates of formula VII above represents triflyloxy, the relevant compound may be prepared by reacting the corresponding compound of formula VII wherein $L^2$ is hydroxy with N-phenyltriflylimide, typically in the presence of triethylamine; or with triflic anhydride, typically in the presence of pyridine. Analogous conditions may be utilised for converting an intermediate of formula VI above wherein $L^2$ represents hydroxy into the corresponding compound wherein $L^2$ represents triflyloxy.

The intermediates of formula VII above wherein $L^2$ is hydroxy may suitably be prepared from the appropriate methoxy-substituted precursor of formula VIII:

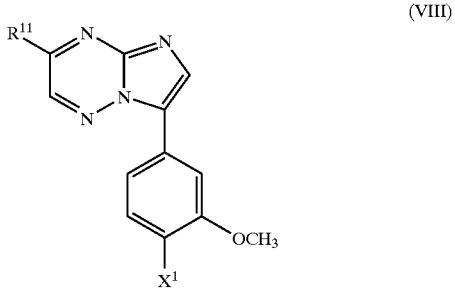

(VIII)

wherein $X^1$ and $R^{11}$ are as defined above; by treatment with boron tribromide, typically in chloroform; or with hydrogen bromide, typically in acetic acid at reflux.

The intermediates of formula VIII above may be prepared by reacting a compound of formula II as defined above with the appropriate compound of formula IX:

(IX)

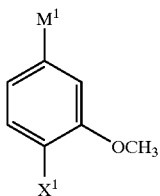

wherein $X^1$ and $M^1$ are as defined above; in the presence of a transition metal catalyst; under conditions analogous to those described above for the reaction between compounds II and III.

Where $L^1$ in the intermediates of formula II above represents bromo, this compound may be prepared by bromination of the corresponding compound of formula X:

(X)

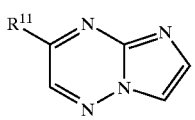

wherein $R^{11}$ is as defined above; typically by treatment with bromine in acetic acid, in the presence of sodium acetate and optionally also potassium bromide.

The intermediates of formula X may be prepared by reacting bromoacetaldehyde with the requisite compound of formula XI:

(XI)

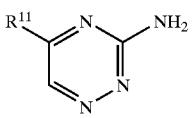

wherein $R^{11}$ is as defined above.

The reaction is conveniently carried out by heating the reactants in 1,2-dimethoxyethane, or a lower alkanol such as methanol and/or ethanol, at a temperature typically in the region of 60–80° C.

In a still further procedure, the compounds according to the present invention may be prepared by a process which comprises reacting a compound of formula XI as defined above with a compound of formula XII:

(XII)

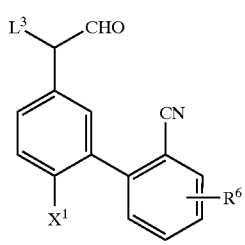

wherein $X^1$ and $R^6$ are as defined above, and $L^3$ represents a suitable leaving group; under conditions analogous to those described above for the reaction between bromoacetaldehyde and compound XI.

The leaving group $L^3$ is suitably a halogen atom, e.g. bromo.

In a yet further procedure, the compounds according to the present invention wherein $X^1$ represents hydrogen and $R^{11}$ represents a heteroaryl moiety may be prepared by a process which comprises reacting a compound of formula XIII with a compound of formula XIV:

(XIII)

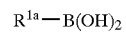

(XIV)

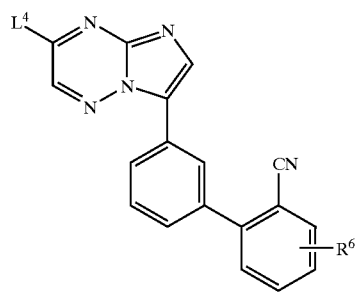

wherein $R^6$ is as defined above, $R^{1a}$ represents a heteroaryl moiety, and $L^4$ represents a suitable leaving group; in the presence of a transition metal catalyst.

The leaving group $L^4$ is typically a halogen atom, e.g. chloro.

The transition metal catalyst of use in the reaction between compounds XIII and XIV is suitably tris(dibenzylideneacetone)-dipalladium(0), in which case the reaction is conveniently effected at an elevated temperature in a solvent such as 1,4-dioxane, typically in the presence of tri-tert-butylphosphine and cesium carbonate.

Where $L^4$ in the compounds of formula XIV above represents a halogen atom, these compounds correspond to compounds of formula I as defined above wherein $R^{11}$ represents halogen, and they may therefore be prepared by any of the methods described above for the preparation of the compounds according to the invention.

Where they are not commercially available, the starting materials of formula V, IX, XI and XII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^{11}$ represents $C_{2-6}$ alkoxycarbonyl initially obtained may be reduced with lithium aluminium hydride to the corresponding compound of formula I wherein $R^{11}$ represents hydroxymethyl. The latter compound may then be oxidised to the corresponding compound of formula I wherein $R^{11}$ represents formyl by treatment with manganese dioxide. The formyl derivative thereby obtained may be condensed with a hydroxylamine derivative of formula $H_2N$—$OR^5$ to provide a compound of formula I wherein $R^{11}$ represents —CH=NOR$^5$. Alternatively, the compound of formula I wherein $R^{11}$ represents formyl may be reacted with a Grignard reagent of formula $R^aMgBr$, wherein $R^a$ represents $C_{1-5}$ alkyl, to afford a compound of formula I wherein $R^{11}$ represents —CH(OH)$R^a$, and this compound may in turn be oxidised using manganese dioxide to the corresponding compound of formula I wherein $R^{11}$ represents —COR$^a$. The latter compound may then be condensed with a hydroxylamine derivative of formula $H_2N$—$OR^5$ to provide a compound of formula I wherein $R^{11}$ represents —CR$^a$=NOR$^5$.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form,. or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 and/or α3 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

Preparative Example A

7-Bromo-3-trifluoromethylimidazo[1,2-b][1,2,4]triazine a) 3-Amino-5-trifluoromethyl-1,2,4-triazine To a stirred solution of sodium acetate trihydrate (22.62 g, 166.2 mmol) in water (80 ml) was added 1,1-dibromo-3,3,3-trifluoroacetone (21.57 g, 79.9 mmol). The solution was heated at reflux under nitrogen for 30 min, then allowed to cool to room temperature before adding solid aminoguanidine bicarbonate (10.88 g, 79.9 mmol). The resulting pale yellow solution (pH 5) was stirred at room temperature for 3 h, then 4 N aqueous NaOH solution (40 ml, 160 mmol) was added causing a precipitate to appear. The mixture (pH 10) was stirred under nitrogen for a further 39 h. The solid was collected by filtration, washed with water and dried at 60° C. under vacuum to give 6.96 g of a mixture of two isomers in a 28:72 ratio. This was further purified by flash chromatography (silica gel, 30% EtOAc/isohexane), then recrystallised from ethanol to afford 3.53 g (27%) of the title compound: $^1$H NMR (400 MHz, DMSO-$d_6$) δ8.00 (2H, br s), 9.08 (1H, s).

b) 3-Trifluoromethylimidazo[1,2-b][1,2,4]triazine

A stirred mixture of bromoacetaldehyde diethyl acetal (2.30 ml, 14.8 mmol) in concentrated hydrobromic acid (0.73 ml) and water (0.73 ml) was heated at reflux for 2 h, then poured into ethanol (25 ml). The solution was neutralised to pH 7 with solid sodium hydrogencarbonate, then filtered. To the filtrate was added 3-amino-5-trifluoromethyl-1,2,4-triazine (1.0079 g, 6.14 mmol) and the mixture was stirred at 60° C. for 20 h, then 80° C. for 23 h. The mixture was evaporated in vacuo, and the residue was purified by flash chromatography (silica gel, 35–50% EtOAc/isohexane) to give 0.2593 g (22%) of the title compound: $^1$H NMR (360 MHz, CDCl$_3$) δ8.20 (1H, d, J 0.8 Hz), 8.30 (1H, d, J 0.9 Hz), 8.73 (1H, s).

c) 7-Bromo-3-trifluoromethylimidazo[1,2-b][1,2,4]triazine

To a solution of 3-trifluoromethylimidazo[1,2-b][1,2,4]triazine (0.2211 g, 1.18 mmol) in acetic acid (6 ml) was added sodium acetate (0.1470 g, 1.79 mmol), then bromine (90.8 μl, 1.76 mmol). The solution was stirred at room temperature for 6 h, then partitioned between saturated aqueous NaHCO$_3$ (100 ml) and ethyl acetate (100 ml). The aqueous layer (pH 9) was further extracted with ethyl acetate (100 ml), and the combined organic extracts were dried (Na$_2$SO$_4$) and evaporated in vacuo. The residue was purified by flash chromatography (silica gel, 25% EtOAc/isohexane) to afford 0.2073 g (66%) of the title compound: $^1$H NMR (360 MHz, CDCl$_3$) δ8.30 (1H, s), 8.83 (1H, s).

Preparative Example B
2-(2-Fluoro-5-nitrophenyl)-4,4,5,5-tetramethyl-[1,3,2]dioxaborolane A mixture of 2-bromo-1-fluoro-4-nitrobenzene (A. Groweiss, *Org. Process Res. Dev.*, 2000, 4, 30–33) (50.10 g, 0.228 mol), dried potassium acetate (44.70 g, 0.455 mol) and bis(pinacolato)diboron (59.16 g, 0.233 mol) in 1,4-dioxane (539 ml) and dimethylsulfoxide (11 ml) was degassed by bubbling nitrogen through the mixture for 1 h. Dichloro[1,1'-bis(diphenylphosphino)ferrocene]palladium(II) dichloromethane adduct (5.58 g, 6.83 mmol) was added and the mixture was stirred at 90° C. under nitrogen for 18.5 h, adding more bis(pinacolato)diboron (7.34 g, 0.029 mol) after 2.5 h. After allowing to cool, the mixture was filtered through glass fibre paper, and the solid was washed with a little dichloromethane. The combined filtrates were evaporated in vacuo and the residue was partitioned between 2 M aqueous NaOH (800 ml) and diethyl ether (800 ml). The aqueous layer was then acidified to pH 6 with concentrated hydrochloric acid (120 ml), causing a solid to precipitate. After leaving in a fridge for 3 days, the solid was collected by filtration, washed with water and dried under vacuum to leave 54.82 g (90%) of 2-(2-fluoro-5-nitrophenyl)-4,4,5,5-tetramethyl-[1,3,2]dioxaborolane: $^1$H NMR (360 MHz, DMSO-$d_6$) δ1.33 (12H, s), 7.48 (1H, m), 8.40–8.45 (2H, m).

Preparative Example C
3-(1-Fluoro-1-methylethyl)-7-[4-fluoro-3-(pyridin-3-yl)phenyl]imidazo[1,2-b][1,2,4]triazine, dihydrochloride salt a) 3-Methyl-3-fluoro-2-butanone This was prepared from 3-bromo-3-methyl-2-butanone as described by Fry and Migron (*Tetrahedron Lett.*, 1979, 3357–3360) to give, after distillation using a Vigreux column, a 47% yield of a 94:6 mixture of the title compound and 3-methyl-3-buten-2-one as a colourless oil: bp 74–6° C.; $^1$H NMR (360 MHz, CDCl$_3$) δ1.45 (6H, d, J 21.5 Hz), 2.28 (3H, d, J 5.0 Hz).

b) 1,1-Dibromo-3-fluoro-3-methyl-2-butanone

To a stirred solution of 3-methyl-3-fluoro-2-butanone (0.1031 g, 0.990 mmol) in anhydrous dichloromethane (5 ml) under nitrogen was added solid pyridinium tribromide (0.7035 g, 1.98 mmol) and the mixture was stirred at room temperature for 18 h. The mixture was then diluted with dichloromethane (5 ml), washed with dilute aqueous sodium hydrogensulfite (10 ml), then saturated aqueous NaCl (10 ml), dried (Na$_2$SO$_4$) and evaporated under low vacuum with no heat. The residue was purified by flash chromatography [silica gel, 5% Et$_2$O/petroleum ether (40–60° C.)] to afford 0.1869 g (72%) of the title compound as a colourless oil: $^1$H NMR (360 MHz, CDCl$_3$) δ1.65 (6H, d, J 21.5 Hz), 6.51 (1H, d, J 1.5 Hz).

c) 3-Amino-5-(1-fluoro-1-methylethyl)-1,2,4-triazine

This was prepared in 45% yield as a single isomer by a similar procedure to that described in Example A, step a, except using 1,1-dibromo-3-fluoro-3-methyl-2-butanone instead of 1,1-dibromo-3,3,3-trifluoroacetone: $^1$H NMR (360 MHz, DMSO-$d_6$) δ1.63 (6H, d, J 8.0 Hz), 7.32 (2H, br s), 8.73 (1H, d, J 1.0 Hz); MS (ES$^+$) m/z 157 [M+H]$^+$.

d) 3-(1-Fluoro-1-methylethyl)imidazo[1,2-b][1,2,4]triazine

A stirred mixture of bromoacetaldehyde diethyl acetal (1.20 ml, 7.73 mmol) in concentrated hydrobromic acid (0.38 ml) and water (0.38 ml) was heated at reflux for 40 min, then poured into ethanol (3 ml). The solution was neutralised to pH 7 with solid sodium hydrogencarbonate, then filtered, washing the solid with more ethanol (3 ml). To the filtrate was added 3-amino-5-(1-fluoro-1-methylethyl)-1,2,4-triazine (1.0046 g, 6.43 mmol) and the mixture was stirred at 70–80° C. for 17 h. The mixture was evaporated in vacuo, and the residue was purified by flash chromatography (silica gel, 70% EtOAc/isohexane to 15% MeOH/EtOAc, then 20% EtOAc/CH$_2$Cl$_2$) to give 0.2000 g (17%) of the title compound as a pale yellow solid: $^1$H NMR (360 MHz, CDCl$_3$) δ1.82 (6H, d, J 22.1 Hz), 7.97 (1H, d, J 1.3 Hz), 7.99 (1H, d, J 1.2 Hz), 8.69 (1H, d, J 1.0 Hz).

e) 7-Bromo-3-(1-fluoro-1-methylethyl)imidazo[1,2-b][1,2,4]triazine

This was prepared in 92% yield by a similar procedure to that described in Example A, step c, except using 3-(1-fluoro-1-methylethyl)imidazo[1,2-b][1,2,4]triazine instead of 3-trifluoromethylimidazo[1,2-b][1,2,4]triazine: $^1$H NMR (360 MHz, CDCl$_3$) δ1.82 (6H, d, J 22.1 Hz), 7.99 (1H, s), 8.81 (1H, d, J 1.1 Hz).

f) 3-(1-Fluoro-1-methylethyl)-7-[4-fluoro-3-(pyridin-3-yl)phenyl]imidazo[1,2-b][1,2,4]triazine, dihydrochloride salt To a solution of 2-bromo-1-fluoro-4-nitrobenzene (A. Groweiss, *Org. Process Res. Dev.*, 2000, 4, 30–33) in tetrahydrofuran (75 ml) and ethanol (75 ml) was added tin(II) chloride dihydrate and the mixture left to stir at ambient temperature for 4 h. The solvent was evaporated and the residue was treated with ice-cold 2 N sodium hydroxide solution (200 ml). The resulting slurry was stirred for 30 min then extracted with dichloromethane (3×200 ml). The combined organic phase was washed with water (200 ml) and brine (200 ml), dried (MgSO$_4$), filtered and evaporated to give 3-bromo-4-fluorophenylamine (7.92 g, 92%) as a yellow oil: $^1$H NMR (360 MHz, CDCl$_3$) δ3.53 (2H, s), 6.53–6.57 (1H, m), 6.83–6.85 (1H, m), 6.90 (1H, dd, J 9, 9 Hz).

A mixture of 3-bromo-4-fluorophenylamine (7.92 g, 41.7 mmol), diethyl(3-pyridyl)borane (6.74 g, 45.9 mmol), tetrakis(triphenylphosphine)palladium(0) (0.96 g, 0.83 mmol) and potassium carbonate (17.26 g, 125 mmol) in 1,2-dimethoxyethane (30 ml) and water (15 ml) was heated at 80° C. for 20 h. After cooling to ambient temperature the reaction was partitioned between ethyl acetate (500 ml) and water (500 ml). The organics were washed with brine (400 ml), dried (Na$_2$SO$_4$), filtered and concentrated in vacuo. Purification of the residue by flash chromatography (silica gel, 0%–20% EtOAc/CH$_2$Cl$_2$) gave 4-fluoro-3-(pyridin-3-yl)phenylamine (3.64 g, 46%) as a colourless oil that solidified on standing to afford a white solid: $^1$H NMR (360 MHz, CDCl$_3$) δ3.65 (2H, s), 6.65–6.72 (2H, m), 6.99. (1H, dd, J 9, 9 Hz), 7.33–7.37 (1H, m), 7.84–7.86 (1H, m), 8.58 (1H, d, J 4 Hz), 8.76 (1H, m).

A warm solution of 4-fluoro-3-(pyridin-3-yl)phenylamine (3.64 g, 19.3 mmol) in 1,4-dioxane (10 ml) was treated with a solution of 48% aqueous hydrobromic acid (100 ml). The resulting suspension was cooled to 0° C. before being treated dropwise over 20 min with a solution of sodium nitrite (1.53 g, 22.2 mmol) in water (4 ml). After stirring at 0° C. for 2 h, a cooled (0° C.) solution of copper(I) bromide (8.31 g, 57.9 mmol) in 48% aqueous hydrobromic acid (30 ml) was added to the reaction which was stirred at 0° C. for 10 min then heated at 50° C. for 20 min. The reaction was cooled to ambient temperature, poured onto ice-cold concentrated ammonia (500 ml) and the product was extracted into ethyl acetate (500 ml). The organics were washed with water (300 ml) and brine (300 ml), dried (Na$_2$SO$_4$), filtered and concentrated in vacuo to give a dark oil. Purification by dry flash column chromatography (silica gel, 10–30% EtOAc/isohexane) gave 3-(5-bromo-2-fluorophenyl)pyridine (3.1 g, 64%) as a white solid: $^1$H NMR (360 MHz, CDCl$_3$) δ7.09 (1H, dd, J 9, 1 Hz), 7.37–7.40 (1H, m), 7.46–7.51 (1H, m), 7.56–7.59 (1H, m), 7.83–7.86 (1H, m), 8.63–8.65 (1H, m), 8.77–8.79 (1H, m).

3-(5-Bromo-2-fluorophenyl)pyridine (3.1 g, 12.3 mmol), potassium acetate (3.62 g, 36.9 mmol) and bis(pinacolato) diboron (3.75 g, 14.8 mmol) were dissolved in 1,4-dioxane (40 ml) and dimethylsulfoxide (0.8 ml) and the mixture degassed with $N_2$ for 15 min. Dichloro[1,1'-bis (diphenylphosphino)ferrocene]palladium(II) dichloromethane adduct (300 mg, 0.37 mmol) was added and the mixture heated at 90° C. for 18 h. The mixture was cooled to ambient temperature-and partitioned between diethyl ether (200 ml) and 2 N hydrochloric acid (50 ml). The organics were discarded and the aqueous phase adjusted to pH 8 by the addition of 4 N sodium hydroxide solution and extracted with diethyl ether (2×500 ml). The organic layer was washed with brine (50 ml), dried ($Na_2SO_4$), filtered and pre-adsorbed onto silica. Purification by flash column chromatography (silica gel, 25% EtOAc/isohexane) gave 3-[2-fluoro-5-(4,4,5,5-tetramethyl-[1,3,2]dioxaborolan-2-yl) phenyl]pyridine (2.64 g, 72%) as a yellow oil that crystallised on standing: $^1$H NMR (36.0 MHz, $CDCl_3$) δ1.35 (12H, s), 7.20 (1H, dd, J 10, 8 Hz), 7.35–7.39 (1H, m), 7.81–7.91 (3H, m), 8.61 (1H, dd, J 5, 2 Hz), 8.82 (1H, s).

A stirred mixture of 7-bromo-3-(1-fluoro-1-methylethyl) imidazo[1,2-b][1,2,4]triazine (0.1059 g, 0.409 mmol) and 3-[2-fluoro-5-(4,4,5,5-tetramethyl-[1,3,2]dioxaborolan-2-yl)phenyl]pyridine (0.1832 g, 0.612 mmol) in 1,2-dimethoxyethane (2 ml) and 2 M aqueous $Na_2CO_3$ (0.613 ml, 1.23 mmol) was degassed by bubbling through nitrogen for 15 min. Tetrakis(triphenylphosphine)palladium(0) (23.4 mg, 0.020 mmol) was then added and the mixture was stirred at 80° C. for 16 h under nitrogen. The mixture was partitioned between ethyl acetate (25 ml) and water (10 ml) and the aqueous phase was extracted further with ethyl acetate (2×25 ml). The organic extracts were combined, dried ($Na_2SO_4$) and evaporated in vacuo. The residue was purified by flash chromatography (silica gel, EtOAc) to yield 0.1047 g (73%) of the title compound as a yellow oil. The hydrochloride salt was prepared in diethyl ether: mp 113–126° C.; $^1$H NMR (400 MHz, DMSO-$d_6$) δ1.81 (6H, d, J 22.2 Hz), 7.68 (1H, dd, J 10.6, 8.6 Hz), 8.03 (1H, dd, J 7.8, 5.5 Hz), 8.36 (1H, m), 8.43 (1H, dd, J 7.4, 2.3 Hz), 8.63 (1H, dd, J 7.4, 1.2 Hz), 8.67 (1H, s), 8.91 (1H, d, J 4.3 Hz), 9.07 (1H, d, J 0.8 Hz), 9.16 (1H, s); MS ($ES^+$) m/z 352 [M+H]$^+$. Anal. Found: C, 51.65; H, 4.48; N, 15.28%. Required for $C_{19}H_{15}F_2N_5 \cdot 2HCl \cdot 0.07C_4H_{10}O \cdot H_2O$: C, 51.75; H, 4.44; N, 15.65%.

Example 1

4,2'-Difluoro-5'-[3-(1-fluoro-1-methylethyl)imidazo[1,2-b][1,2,4]triazin-7-yl]biphenyl-2-carbonitrile A mixture of 2-bromo-5-fluorobenzonitrile (20 g, 100 mmol), 2-(2-fluoro-5-nitrophenyl)-4,4,5,5-tetramethyl-[1,3,2]dioxaborolane (from Example B) (34.7 g, 130 mmol) and potassium fluoride (19.2 g, 330 mmol) in tetrahydrofuran (350 ml) and water (20 ml) was degassed with nitrogen for 30 min then treated with tris(dibenzylideneacetone)dipalladium(0) (1.83 g, 2 mmol) followed by tri-tert-butylphosphine (4 ml of a 0.2 M solution in 1,4-dioxane, 0.8 mmol). This mixture was stirred at ambient temperature for 30 min before heating at 50° C. for 18 h. The resulting dark suspension was cooled to ambient temperature, diluted with 0.5 M sodium hydroxide (2.5 l) and stirred at ambient temperature for 4 h. The solid was collected by filtration, washed with water and dried under suction to afford 4,2'-difluoro-5'-nitrobiphenyl-2-carbonitrile as a black solid (28.1 g, >100%) contaminated with dibenzylideneacetone: $^1$H NMR (360 MHz, $CDCl_3$) δ7.38–7.56 (4H, m), 8.33–8.40 (2H, m).

A suspension of 4,2'-difluoro-5'-nitrobiphenyl-2-carbonitrile (26 g, 100 mmol) in ethanol (180 ml) and ethyl acetate (180 ml) was treated with platinum(IV) oxide (1.02 g, 4.5 mmol) and then shaken under an atmosphere of hydrogen (40 psi) for 1 h. [The reaction was very exothermic and complete solution is brought about by the increase in temperature]. The catalyst was removed by filtration through glass microfibre filter paper [if any crystalline product is present the filter cake is washed with dichloromethane] and the filtrate evaporated to dryness to afford 5'-amino-4,2'-difluorobiphenyl-2-carbonitrile as a straw-coloured solid (23 g, 100%): $^1$H NMR (360 MHz, $CDCl_3$) δ3.66 (2H, s), 6.66–6.70 (1H, m), 6.71–6.74 (1H, m), 7.00 (1H, dd, J 9, 9 Hz), 7.33–7.38 (1H, m), 7.44–7.49 (1H, m).

5'-Amino-4,2'-difluorobiphenyl-2-carbonitrile (23 g, 100 mmol) was dissolved in hot 1,4-dioxane (20 ml) then treated with a chilled (5° C.) solution of hydrobromic acid (200 ml of a 48% solution in water). The resulting suspension was cooled to 2° C. (internal temperature) before adding a solution of sodium nitrite (6.9 g, 100 mmol) in water (14 ml) at such a rate that the internal temperature did not exceed 4° C. Once addition was complete the reaction was stirred at <4° C. for 1 h before pouring the reaction into a cooled (5° C.) solution of copper(I) bromide (21.5 g, 150 mmol) in 48% aqueous hydrobromic acid (75 ml). The resulting dark mixture was left to stir at ambient temperature for 15 min then heated at 50° C. for 40 min. After cooling to ambient temperature the mixture was diluted with water (1l) and then extracted with ethyl acetate (2×400 ml). The organics were combined then washed with 10% ammonium hydroxide (500 ml), water (500 ml), brine (400 ml) and, dried ($MgSO_4$). Filtration and evaporation to dryness gave a brown oil, which crystallised on standing. Purification of this residue by dry flash chromatography (silica gel, 2–4% EtOAc/isohexane) furnished 5'-bromo-4,2'-difluorobiphenyl-2-carbonitrile as a white solid (27.5 g, 94%): $^1$H NMR (360 MHz, $CDCl_3$) δ7.11 (1H, dd, J 9, 9 Hz), 7.37–7.58 (5H, m).

A mixture of 5'-bromo-4,2'-difluorobiphenyl-2-carbonitrile (1.26 g, 4.3 mmol), potassium acetate (1.26 g, 12.8 mmol) and bis(neopentyl glycolato)diboron (1.07 g, 4.7 mmol) in 1,4-dioxane containing 2% v/v dimethylsulfoxide (20 ml) was degassed with nitrogen for 10 min. Dichloro[1,1'-bis(diphenylphosphino)ferrocene]palladium(II) dichloromethane adduct (105 mg, 0.13 mmol) was then added and the mixture heated at 90° C. for 16 h. After cooling to ambient temperature the reaction mixture was filtered to remove inorganics and the filter cake was washed with diethyl ether. The filtrate was evaporated to dryness and the residue stirred with ice-cold 2 N sodium hydroxide solution (50 ml) for 45 min. This basic mixture was washed with diethyl ether and the organics discarded. The pH of the aqueous phase was adjusted to 5 with 36% hydrochloric acid then extracted with diethyl ether (50 ml). The organic phase was washed with brine, dried ($MgSO_4$), filtered and concentrated in vacuo to give 5'-(5,5-dimethyl-[1,3,2] dioxaborinan-2-yl)-4,2'-difluoro-biphenyl-2-carbonitrile as a brown oil which crystallised on standing (1.15 g, 82%): $^1$H NMR (360 MHz, $CDCl_3$) δ1.03 (6H, s), 3.76 (4H, s), 7.20 (1H, dd, J 10, 8 Hz), 7.33–7.38 (1H, m), 7.44–7.50 (2H, m), 7.81 (1H, dd, J 8, 2 Hz), 7.85–7.90 (1H, m).

5'-(5,5-Dimethyl-[1,3,2]dioxaborinan-2-yl)-4,2'-difluorobiphenyl-2-carbonitrile was coupled to 7-bromo-3-(1-fluoro-1-methylethyl)imidazo[1,2-b][1,2,4]triazine in 77% yield using a similar procedure to that described in Example C, step f, to give a yellow solid: mp 156–159° C. (EtOAc-isohexane); $^1$H NMR (400 MHz, $CDCl_3$) δ1.84 (6H, d, J 22.0 Hz), 7.36–7.46 (2H, m), 7.54 (1H, dd, J7.8, 2.7 Hz), 7.57–7.60 (1H, m), 8.10–8.16 (2H, m), 8.30 (1H, s), 8.79 (1H, d, J 1.2 Hz); MS (ES+) m/z 394 [M+H]+. Anal. Found: C, 64.07; H, 3.66; N, 17.60%. Required for $C_{21}H_{14}F_3N_5$: C, 64.12; H, 3.59; N, 17.80%.

Example 2
5,2'-Difluoro-5'-(3-trifluoromethylimidazo[1,2-b][1,2,4]triazin-7-yl)-biphenyl-2-carbonitrile
a) 5,2'-Difluoro-5'-nitrobiphenyl-2-carbonitrile A suspension of 2-bromo-4-fluorobenzonitrile (2.50 g, 12.5. mmol), potassium fluoride (2.40 g, 41.3 mmol) and 2-(2-fluoro-5-nitrophenyl)-4,4,5,5-tetramethyl-[1,3,2](4.67 g, 17.5 mmol) in tetrahydrofuran (50 ml) was degassed with nitrogen for 30 min. Tris(dibenzylideneacetone)dipalladium (0) and tri-tert-butylphosphine (0.2 M solution in 1,4-dioxane, 3.7 ml) were added and the mixture stirred at ambient temperature for 15 min then at 50° C. for 18 h. After cooling to ambient temperature, the resulting dark suspension was poured onto 0.5 M sodium hydroxide solution (500 ml) and stirred vigorously for 2 h. The dark solid was collected by filtration, washed with water (100 ml) and isohexane (50 ml) and left to air dry which gave the title compound as a brown/black solid: $^1$H NMR (360 MHz, $CDCl_3$) δ7.25–7.33 (2H, m), 7.40–7.44 (1H, m), 7.86 (1H, dd, J 9, 6 Hz), 8.35–8.42 (2H, m).
b) 5'-Amino-5,2'-difluorobiphenyl-2-carbonitrile 5,2'-Difluoro-5'-nitrobiphenyl-2-carbonitrile (3.25 g, 12.5 mmol) in tetrahydrofuran (20 ml) and ethanol (20 ml) was treated with tin(II) chloride dihydrate (9.86 g, 43.8 mmol) and the mixture left to stir at ambient temperature for 18 h. The solvent was evaporated and the residue stirred with 2 N sodium hydroxide solution (40 ml) for 2 h. The resulting suspension was diluted with water (100 ml) and extracted with dichloromethane (3×200 ml). The combined organics were washed with water (200 ml), brine (200 ml), dried over anhydrous sodium sulfate, filtered and evaporated to give the title compound as a brown solid: $^1$H NMR (360 MHz, $CDCl_3$) δ3.68 (2H, s), 6.67–6.76 (2H, m), 7.02 (1H, dd, J 9, 9 Hz), 7.12–7.27 (2H, m), 7.78 (1H, dd, J9, 6 Hz).
c) 5'-Bromo-5,2'-difluorobiphenyl-2-carbonitrile 5'-Amino-5,2'-difluorobiphenyl-2-carbonitrile (2.87 g, 12.5 mmol) was dissolved in hot 1,4-dioxane (4 ml), 48% aqueous hydrobromic acid (40 ml) was added and the mixture cooled to 0° C. before dropwise addition of sodium nitrite (0.86 g, 12.5 mmol) in water (1.5 ml) over 20 min. The resulting mixture was stirred at 0° C. for 1.5 h then poured onto a cooled (0° C.) solution of copper(I) bromide (5.38 g, 37.5 mmol) in 48% hydrobromic acid (10 ml). The solution was stirred at 0° C. for 15 min then heated at 50° C. for 20 min. The mixture was cooled to ambient temperature, diluted with water (500 ml) and extracted with ethyl acetate (2×300 ml). The combined organics were washed with 10% aqueous ammonia solution (200 ml), water (200 ml) and brine (200 ml), dried over anhydrous magnesium sulfate, filtered and evaporated to give a black solid. Purification by chromatography [silica gel, 2–6% EtOAc/isohexane (containing 0.5% methanol)] gave the title compound as a pale brown solid: $^1$H NMR (400 MHz, $CDCl_3$) δ7.13 (1H, dd, J9, 9 Hz), 7.19–7.23 (2H, m), 7.52–7.60 (2H, m), 7.81 (1H, dd, J8, 5 Hz).
d) 5'-(5,5-Dimethyl-[1,3,2]dioxaborinan-2-yl)-5,2'-difluorobiphenyl-2-carbonitrile A mixture of 5'-bromo-5,2'-difluorobiphenyl-2-carbonitrile (2.48 g, 8.43 mmol), potassium acetate (2.48 g, 25.3 mmol) and bis(neopentyl glycolato)diboron (2.48 g, 11.0 mmol) in 1,4-dioxane (40 ml) containing dimethylsulfoxide (0.8 ml) was degassed with nitrogen for 20 min. Dichloro[1,1'-bis(diphenylphosphino)ferrocene]palladium (II) dichloromethane adduct (200 mg, 0.25 mmol) was then added and the reaction heated at 90° C. for 24 h. The mixture was cooled to ambient temperature then partitioned between 2 N sodium hydroxide (75 ml) and diethyl ether (100 ml) and the organics were discarded. The aqueous extract was made acidic (pH 5) with 36% hydrochloric acid and then extracted with diethyl ether (2×75 ml). The organic extract was washed with water (50 ml) and brine (75 ml), dried over anhydrous magnesium sulfate and evaporated to give 5'-(5,5-dimethyl-[1,3,2]dioxaborinan-2-yl)-5,2'-difluorobiphenyl-2-carbonitrile as a brown oil that crystallised on standing: $^1$H NMR (400 MHz, $CDCl_3$) δ1.03 (6H, s), 3.77 (4H, s), 7.15–7.24 (3H, m), 7.77 (1H, dd, J9, 6 Hz), 7.83 (1H, dd, J8, 2 Hz), 7.87–7.91 (1H, m).

7-Bromo-3-trifluoromethylimidazo[1,2-b][1,2,4]triazine was coupled with 5'-(5,5-dimethyl-[1,3,2]dioxaborinan-2-yl)-5,2'-difluorobiphenyl-2-carbonitrile as described in Example C to give 68.7 mg (46%) of 5,2'-difluoro-5'-(3-trifluoromethylimidazo[1,2-b][1,2,4]triazin-7-yl)biphenyl-2-carbonitrile as a yellow solid: mp 200–201° C.; $^1$H NMR (360 MHz, $CDCl_3$) δ7.25–7.34 (2H, m), 7.44 (1H, t, J8.9 Hz), 7.87 (1H, dd, J5.4, 8.6 Hz), 8.18–8.26 (2H, m), 8.63 (1H, s), 8.82 (1H, s); MS (ES+) m/z 401. Anal. Found: C, 55.98; H, 2.13; N, 17.49%. Required for $C_{19}H_8F_5N_5 \cdot 0.3H_2O$: C, 56.11; H, 2.13; N, 17.22%.

Example 3
4,2'-Difluoro-5'-[3-(1-hydroxy-1-methylethyl)imidazo[1,2-b][1,2,4]triazin-7-yl]biphenyl-2-carbonitrile
a) 1,1-Dibromo-3-hydroxy-3-methylbutan-2-one To a stirred solution of 3-methyl-3-hydroxy-2-butanone (40 g, 0.392 mol) in anhydrous dichloromethane (2.2 l) under nitrogen was added solid pyridinium tribromide (250.4 g, 0.784 mol) in portions and the mixture was stirred at room temperature for 14 h. The mixture was then washed with dilute aqueous sodium hydrogensulfite (500 ml), then saturated aqueous NaCl (500 ml, dried ($Na_2SO_4$), and evaporated in vacuo. The residue was purified by flash chromatography (silica gel, $CH_2Cl_2$) to afford 31.4 g (31%) of the title compound as a colourless oil: $^1$H NMR (360 MHz, $CDCl_3$) δ1.54 (6H, s), 2.45 (1H, br s), 6.62 (1H, s).
b) 2-(3-Amino-[1,2,4]triazin-5-yl)propan-2-ol and 2-(3-amino-[1,2,4]triazin-6-yl)propan-2-ol To a stirred solution of sodium acetate trihydrate (32.9 g, 0.342 mol) in water (90 ml) was added 1,1-dibromo-3-hydroxy-3-methylbutan-2-one (29.6 g, 0.114 mol). The solution was heated at reflux under nitrogen for 30 min, then allowed to cool to room temperature before adding solid aminoguanidine bicarbonate (15.54 g, 0.114 mol). The resulting pale yellow solution (pH 5) was stirred at room temperature for 15 min, then 4 N aqueous NaOH solution (56.9 ml, 0.228 mol) was added and the mixture (pH 10) was stirred under nitrogen for a further 14 h. The solution was continuously extracted with warm dichloromethane over a period of 24 h. After this time the solvent was evaporated to leave a residue which was triturated with diethyl ether to give a solid. The solid was collected by filtration and dried at 60° C. under vacuum to give 8.17 g (47%) of a mixture of two isomers in a 60:40 ratio with the required 2-(3-amino-[1,2,4]triazin-5-yl)propan-2-ol being the major product: NMR (360 MHz, DMSO-$d_6$) δ1.38 (major) and 1.47 (minor) (6H, s), 5.30 (major) and 5.43 (minor) (1H, br s), 7.01 (major) and 7.06 (minor) (2H, br s), 8.43 (major) and 8.80 (minor) (1H, s); MS (ES+) m/z 155 [M+H]+.
c) 2-(Imidazo[1,2-b][1,2,4]triazin-3-yl)propan-2-ol A stirred mixture of bromoacetaldehyde diethyl acetal (16.5 ml, 0.106 mol) in concentrated hydrobromic acid (4.13 ml) and water (4.13 ml) was heated at reflux for 40 min, then-poured into ethanol (175 ml). The solution was neutralised to pH 7 with solid sodium hydrogencarbonate, then filtered, washing the solid with more ethanol (30 ml). To the filtrate was added a 60:40 mixture of 2-(3-amino-[1,2,4]triazin-5-yl)propan-2-ol and 2-(3-amino-[1,2,4]triazin-6-yl)propan-2-ol (8.17 g, 0.053 mol) and the mixture was stirred at reflux temperature for 6 h. The mixture was evaporated in vacuo, and the residue was triturated with hot dichloromethane and filtered. The solid which was collected was triturated with hot acetone and collected by filtration again to leave a white solid (14 g). The solid was dissolved in water (30 ml) and continuously extracted with hot dichloromethane over a period of 24 h. The organic layer was separated and concentrated under vacuum to leave a thick yellow oil (3 g) which favoured the required isomer in a ratio of 4:1. The required product was obtained in pure form by flash chromatography (silica gel, 2% MeOH/CH$_2$Cl$_2$) to give 2.12 g (23%) of the title compound as a pale yellow solid: $^1$H NMR (360 MHz, CDCl$_3$) δ1.69 (6H, s), 3.69 (1H, br s), 7.93 (2H, s), 8.70 (1H, s).

d) 2-(7-Bromoimidazo[1,2-b][1,2,4]triazin-3-yl)propan-2-ol

This was prepared in 75% yield by a similar procedure to that described in Example A, step c, except using 2-(imidazo[1,2-b][1,2,4]triazin: $^1$H NMR (360 MHz, CDCl$_3$) δ1.70 (6H, s), 3.12 (1H, br s), 7.95 (1H, s), 8.80 (1H, s).

e) 4,2'-Difluoro-5'-[3-(1-hydroxy-1-methylethyl)imidazo[1,2-b][1,2,4]triazin-7-yl]biphenyl-2-carbonitrile 5'-(5,5-Dimethyl-[1,3,2]dioxaborinan-2-yl)-4,2'-difluorobiphenyl-2-carbonitrile (see Example 1) was coupled to 2-(7-bromoimidazo[1,2-b][1,2,4]triazin-3-yl)propan-2-ol in 54% yield using a similar procedure to that described in Example C, step f, to give a yellow solid: mp 215° C.; $^1$H NMR (360 MHz, CDCl$_3$) δ1.71 (6H, s), 3.27 (1H, br s), 7.35–7.59 (4H, m), 8.09–8.15 (2H, m), 8.26 (1H, s), 8.78 (1H, s); MS (ES$^+$) m/z 392 [M+H]$^+$. Anal. Found: C, 64.38; H, 3.88; N, 17.66%. Required for C$_{21}$H$_{15}$F$_2$N$_5$O: C, 64.45; H, 3.86; N, 17.89%.

Example 4
4-Fluoro-3'-[3-(1-hydroxy-1-methylethyl)imidazo[1,2-b][1.2,4]triazin-7-yl]-biphenyl-2-carbonitrile 2-Bromo-5-fluorobenzonitrile and 3-nitrophenylboronic acid were coupled following the procedure in Example 1 to afford 4-fluoro-3'-nitro-biphenyl-2-carbonitrile as a black solid: $^1$H NMR (360 MHz, CDCl$_3$) δ7.39–7.48 (2H, m), 7.52–7.64 (1H, m), 7.71 (1H, dd, J 8, 8 Hz), 7.89 (1H, d, J 8 Hz), 8.33–8.37 (2H, m).

4-Fluoro-3'-nitrobiphenyl-2-carbonitrile was reduced following the procedure in Example 1 to give 3'-amino-4-fluorobiphenyl-2-carbonitrile as a brown solid: $^1$H NMR (400 MHz, CDCl$_3$) δ6.76 (1H, ddd, J 8, 2, 2 Hz), 6.80 (1H, dd, J 2, 2 Hz), 6.87 (1H, ddd, J 8, 1, 1 Hz), 7.27 (1H, dd, J 8, 8 Hz), 7.35 (1H, ddd, J8, 8, 3 Hz), 7.41–7.51 (2H, m).

3'-Amino-4-fluorobiphenyl-2-carbonitrile was bromodeaminated following the procedure in Example 1 to give 3'-bromo-4-fluorobiphenyl-2-carbonitrile as a white solid: $^1$H NMR (400 MHz, CDCl$_3$) δ7.35–7.40 (2H, m), 7.46–7.50 (3H, m), 7.59 (1H, dd, J 2, 1 Hz), 7.64 (1H, dd, J 2, 2 Hz).

3'-Bromo-4-fluorobiphenyl-2-carbonitrile was converted to 4-fluoro-3'-(4,4,5,5-tetramethyl-[1,3,2]dioxaborolan-2-yl)biphenyl-2-carbonitrile following the procedure in Example 1, affording a brown oil that crystallised on standing: $^1$H NMR (400 MHz, CDCl$_3$) δ1.36 (12H, s), 7.32–7.37 (1H, m), 7.43–7.54 (3H, m), 7.63–7.68 (1H, m), 7.88–7.90 (2H, m).

4-Fluoro-3'-(4,4,5,5-tetramethyl-[1,3,2]dioxaborolan-2-yl)biphenyl-2-carbonitrile was coupled to 2-(7-bromoimidazo[1,2-b][1,2,4]triazin-3-yl)-propan-2-ol in 32% yield using a similar procedure to that described in Example C, step f, to give a yellow solid: mp 175° C.; $^1$H NMR (360 MHz, CDCl$_3$) δ1.71 (6H, s), 3.25 (1H, br s), 7.41–7.67 (5H, m), 8.01 (1H, m), 8.24 (1H, s), 8.31 (1H, s), 8.78 (1H, s); MS (ES$^+$) m/z 374 [M+H]$^+$. Anal. Found: C, 67.38; H, 4.27; N, 18.51%. Required for C$_{21}$H$_{16}$FN$_5$O; C, 67.55; H, 4.32; N, 18.76%.

Example 5
6,2'-Difluoro-5'-[3-(1-hydroxy-1-methylethyl)imidazo[1,2-b][1,2,4]triazin-7-yl]biphenyl-2-carbonitrile A mixture of 2,3-difluorobenzonitrile (19.0 g, 137 mmol) and ethanol (200 ml) pre-saturated with ammonia gas was heated at 140° C. in an autoclave for 8 h (terminal pressure 200 psi). The mixture was allowed to cool to ambient temperature and evaporated to dryness. The residue was dissolved in water (400 ml) and extracted with diethyl ether (2×300 ml). The combined organics were washed with water (300 ml) and brine (250 ml), dried over anhydrous magnesium sulfate, filtered and evaporated. Trituration with isohexane (150 ml) afforded 2-amino-3-fluorobenzonitrile (9.8 g, 50%) as an off-white solid: $^1$H NMR (360 MHz, CDCl$_3$) δ4.47 (2H, s), 6.65–6.71 (1H, m), 7.14–7.20 (2H, m).

2-Amino-3-fluorobenzonitrile (9.8 g, 71.9 mmol) was bromo-deaminated as described in Example 1 to afford 2-bromo-3-fluorobenzonitrile as a pale brown solid: $^1$H NMR (360 MHz, CDCl$_3$) δ7.62–7.68 (1H, m), 7.74–7.85 (1H, ddd, J 9, 9, 1 Hz), 7.74–7.85 (1H, ddd, J 8, 1, 1 Hz).

2-Bromo-3-fluorobenzonitrile (2.50 g, 12.5 mmol) was coupled to 2-(2-fluoro-5-nitrophenyl)-4,4,5 5-tetramethyl-[1,3,2]dioxaborolane as described in Example 1 to give 6,2'-difluoro-5'-nitrobiphenyl-2-carbonitrile as a black solid: $^1$H NMR (360 MHz, CDCl$_3$) δ7.40–7.44 (1H, m), 7.47–7.52 (1H, m), 7.59–7.67 (2H, m), 8.37–8.44 (2H, m).

6,2'-Difluoro-5'-nitrobiphenyl-2-carbonitrile (3.25 g, 12.5 mmol) was reduced using the procedure described in Example 1 to give 5'-amino-6,2'-difluorobiphenyl-2-carbonitrile as a brown oil: $^1$H NMR (360 MHz, CDCl$_3$) δ3.74 (2H, s), 6.68 (1H, m), 6.73–6.77 (1H, m), 7.02 (1H, dd, J 9, 9 Hz), 7.37–7.49 (2H, m), 7.56–7.65 (1H, m).

5'-Amino-6,2'-difluorobiphenyl-2-carbonitrile was bromo-deaminated as described in Example 1 to furnish 5'-bromo-6,2'-difluorobiphenyl-2-carbonitrile as a pale brown solid: $^1$H NMR (360 MHz, CDCl$_3$) δ7.13 (1H, dd, J 9, 9 Hz), 7.37–7.49 (2H, ddd, J 9, 9, 1 Hz), 7.57–7.62 (4H, m).

5'-Bromo-6,2'-difluorobiphenyl-2-carbonitrile was converted to 6,2'-difluoro-5'-(4,4,5,5-tetramethyl-[1,3,2]dioxaborolan-2-yl)biphenyl-2-carbonitrile using the procedure described in Example 1. This gave a brown oil that crystallised on standing: $^1$H NMR (360 MHz, CDCl$_3$) δ1.34 (12H, s), 7.21 (1H, dd, J8, 2 Hz), 7.38–7.51 (2H, m), 7.57–7.59 (1H, m), 7.85 (1H, dd, J 8, 2 Hz), 7.90–7.94 (1H, m).

6,2'-Difluoro-5'-(4,4,5,5-tetramethyl-[1,3,2]dioxaborolan-2-yl)-biphenyl-2-carbonitrile was coupled to 2-(7-bromoimidazo[1,2-b][1,2,4]triazin-3-yl)propan-2-ol in 32% yield using a similar procedure to that described in Example C, step f, to give a yellow solid: mp 206° C.; $^1$H NMR (360 MHz, CDCl$_3$) δ1.71 (6H, s), 3.28 (1H, br s), 7.37–7.66 (4H, m), 8.15 (2H, m), 8.26 (1H, s), 8.78 (1H, s); MS (ES$^+$) mn/z 392 [M+H]$^+$. Anal. Found: C, 64.66; H, 3.93, N, 17.71%. Required for C$_{21}$H$_{15}$F$_2$N$_5$O: C, 64.45; H, 3.86; N, 17.89%.

What is claimed is:

1. A method for the treatment or prevention of convulsions or migraine which comprises administering to a patient in need thereof an effective amount of a compound of the formula I:

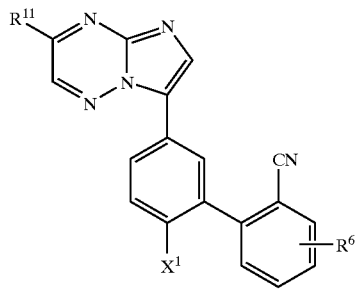

(I)

wherein:

X$^1$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$, or a heteroaryl selected from the group consisting of: pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl;

R$^4$ represents hydrogen or C$_{1-6}$ alkyl;

R$^5$ represents hydrogen, C$_{1-6}$ alkyl, hydroxy(C$_{1-6}$)alkyl or di(C$_{1-6}$)alkylamino(C$_{1-6}$)alkyl; and R$^6$ represents fluoro, or a pharmaceutically acceptable salt thereof.

2. The method of claim 1 wherein the compound of formula I the fluorine atom R$^6$ is attached to the phenyl ring at the 6-position (relative to the cyano group at position 2).

3. The method of claim 1 wherein the compound of formula I X$^1$ represents fluorine.

4. The method of claim 1 wherein the compound of formula I R$^{11}$ represents 2-hydroxyprop-2-yl.

5. The method of claim 1 wherein the compound is selected from the group consisting of:

4,2'-difluoro-5'-[3-(1-fluoro-1-methylethyl)imidazo[1,2-b][1,2,4]triazin-7-yl]biphenyl-2-carbonitrile;

5,2'-difluoro-5'-(3-trifluoromethylimidazo[1,2-b][1,2,4]triazin-7-yl)-biphenyl-2-carbonitrile;

4,2'-difluoro-5'-[3-(1-hydroxy-1-methylethyl)imidazo[1,2-b][1,2,4]triazin-7-yl]biphenyl-2-carbonitrile;

4-fluoro-3'-[3-(1-hydroxy-1-methylethyl)imidazo[1,2-b][1,2,4]triazin-7-yl]-biphenyl-2-carbonitrile;

6,2'-difluoro-5'-[3-(1-hydroxy-1-methylethyl)imidazo[1,2-b][1,2,4]triazin-7-yl]biphenyl-2-carbonitrile;

and pharmaceutically acceptable salts thereof.

6. A method for the treatment of convulsions which comprises administering to a patient in need thereof an effective amount of 6,2'-difluoro-5'-[3-(1-hydroxy-1-methylethyl)imidazo[1,2-b][1,2,4]triazin-7-yl]biphenyl-2-carbonitrile or a pharmaceutically acceptable salt thereof.

7. A method for the prevention of convulsions which comprises administering to a patient in need thereof an effective amount of 6,2'-difluoro-5'-[3-(1-hydroxy-1-methylethyl)imidazo[1,2-b][1,2,4]triazin-7-yl]biphenyl-2-carbonitrile or a pharmaceutically acceptable salt thereof.

8. A method for the treatment of migraine which comprises administering to a patient in need thereof an effective amount of 6,2'-difluoro-5'-[3-(1-hydroxy-1-methylethyl)imidazo[1,2-b][1,2,4]triazin-7-yl]biphenyl-2-carbonitrile or a pharmaceutically acceptable salt thereof.

9. A method for the prevention of migraine which comprises administering to a patient in need thereof an effective amount of 6,2'-difluoro-5'-[3-(1-hydroxy-1-methylethyl)imidazo[1,2-b][1,2,4]triazin-7-yl]biphenyl-2-carbonitrile or a pharmaceutically acceptable salt thereof.

* * * * *